(12) United States Patent
Tse et al.

(10) Patent No.: US 11,986,824 B2
(45) Date of Patent: May 21, 2024

(54) SYSTEM AND METHOD FOR IMMUNE ACTIVITY DETERMINATION

(71) Applicant: CytoVale Inc., San Francisco, CA (US)

(72) Inventors: Henry Tat Kwong Tse, San Francisco, CA (US); Ajay M. Shah, San Francisco, CA (US); Lionel Guillou, San Francisco, CA (US); Roya Sheybani, San Francisco, CA (US); Christopher Dahlberg, San Francisco, CA (US); Anne E. Jensen, San Francisco, CA (US)

(73) Assignee: CytoVale Inc., San Francisco, CA (US)

( * ) Notice: Subject to any disclaimer, the term of this patent is extended or adjusted under 35 U.S.C. 154(b) by 170 days.

(21) Appl. No.: 17/401,627

(22) Filed: Aug. 13, 2021

(65) Prior Publication Data

US 2021/0370301 A1    Dec. 2, 2021

Related U.S. Application Data

(63) Continuation of application No. 16/943,716, filed on Jul. 30, 2020, now Pat. No. 11,123,734.
(Continued)

(51) Int. Cl.
*B01L 3/00* (2006.01)
*G06N 3/02* (2006.01)
*G06T 7/00* (2017.01)

(52) U.S. Cl.
CPC ... *B01L 3/502761* (2013.01); *B01L 3/502715* (2013.01); *B01L 3/502746* (2013.01);
(Continued)

(58) Field of Classification Search
CPC ......... B01L 3/502761; B01L 3/502715; B01L 3/502746; B01L 3/502753;
(Continued)

(56) References Cited

U.S. PATENT DOCUMENTS

| 4,654,312 A | 3/1987 | Chang et al. |
| 4,902,613 A | 2/1990 | Chang et al. |

(Continued)

FOREIGN PATENT DOCUMENTS

| EP | 2619545 B1 | 1/2019 |
| JP | 2001211896 A | 8/2001 |

(Continued)

OTHER PUBLICATIONS

Rosenbluth, Michael J., Wilbur A. Lam, and Daniel A. Fletcher. "Analyzing cell mechanics in hematologic diseases with microfluidic biophysical flow cytometry." Lab on a Chip 8.7 (2008): 1062-1070. (Year: 2008).*

(Continued)

*Primary Examiner* — Robert J Eom
(74) *Attorney, Agent, or Firm* — Jeffrey Schox; Randy Mehlenbacher (57) ABSTRACT

A system and method for determining a trajectory parameter of particles, comprising receiving a plurality of particles at a microfluidic channel, applying a force to each particle of the microfluidic channel, acquiring a dataset of each particle, measuring a trajectory of the particle, and determining a trajectory parameter of the particles.

15 Claims, 5 Drawing Sheets

Related U.S. Application Data (60) Provisional application No. 62/881,283, filed on Jul. 31, 2019.

(52) U.S. Cl.
CPC .......... *B01L 3/502753* (2013.01); *G06N 3/02* (2013.01); *G06T 7/0012* (2013.01); *B01L 2200/0631* (2013.01); *B01L 2200/0652* (2013.01); *B01L 2200/0668* (2013.01); *B01L 2200/0684* (2013.01); *B01L 2200/0694* (2013.01); *B01L 2200/12* (2013.01); *B01L 2300/0877* (2013.01); *B01L 2300/0887* (2013.01); *B01L 2300/185* (2013.01); *B01L 2400/0409* (2013.01); *B01L 2400/0415* (2013.01); *B01L 2400/0436* (2013.01); *G06T 2207/30024* (2013.01); *G06T 2207/30104* (2013.01)

(58) Field of Classification Search
CPC ..... B01L 2200/0631; B01L 2200/0652; B01L 2200/0668; B01L 2200/0684; B01L 2200/0694; B01L 2200/12; B01L 2300/0877; B01L 2300/0887; B01L 2300/185; B01L 2400/0409; B01L 2400/0415; B01L 2400/0436; G06N 3/02; G06T 7/0012; G06T 2207/30024; G06T 2207/30104
See application file for complete search history.

(56) References Cited

U.S. PATENT DOCUMENTS

| | | | |
|---|---|---|---|
| 5,155,044 | A | 10/1992 | Ledis et al. |
| 5,798,827 | A | 8/1998 | Frank et al. |
| 8,935,098 | B2 | 1/2015 | Di Carlo et al. |
| 9,151,705 | B2 | 10/2015 | Di Carlo et al. |
| 9,414,990 | B2 | 8/2016 | Ivosevic et al. |
| 9,464,977 | B2 | 10/2016 | Di Carlo et al. |
| 9,638,620 | B2 | 5/2017 | Di Carlo et al. |
| 9,897,532 | B2 | 2/2018 | Di Carlo et al. |
| 10,107,735 | B2 | 10/2018 | Di Carlo et al. |
| 10,808,219 | B2 | 10/2020 | Masaeli et al. |
| 11,521,706 | B2 | 12/2022 | Xin et al. |
| 11,548,003 | B1 | 1/2023 | Tse et al. |
| 2005/0070005 | A1 | 3/2005 | Keller |
| 2005/0221396 | A1 | 10/2005 | Simon-Lopez |
| 2006/0139638 | A1 | 6/2006 | Muller et al. |
| 2006/0210438 | A1 | 9/2006 | Nagai et al. |
| 2008/0077072 | A1 | 3/2008 | Keenan et al. |
| 2009/0014360 | A1 | 1/2009 | Toner et al. |
| 2013/0177935 | A1 | 7/2013 | Di et al. |
| 2013/0224851 | A1 | 8/2013 | Ljungmann et al. |
| 2014/0087412 | A1 | 3/2014 | Fouras et al. |
| 2014/0113324 | A1 | 4/2014 | Di Carlo et al. |
| 2014/0227777 | A1 | 8/2014 | Choi et al. |
| 2014/0315287 | A1 | 10/2014 | Di Carlo et al. |
| 2015/0355073 | A1 | 12/2015 | Di Carlo et al. |
| 2016/0231224 | A1 | 8/2016 | Di Carlo et al. |
| 2017/0089822 | A1 | 3/2017 | Di Carlo et al. |
| 2017/0234788 | A1 | 8/2017 | Di Carlo et al. |
| 2017/0284924 | A1 | 10/2017 | Tse et al. |
| 2018/0128735 | A1 | 5/2018 | Di Carlo et al. |
| 2018/0267021 | A1 | 9/2018 | Suresh et al. |
| 2018/0305758 | A1 | 10/2018 | Shi et al. |
| 2019/0092757 | A1 | 3/2019 | Ashford et al. |
| 2019/0143326 | A1 | 5/2019 | Irimia et al. |
| 2021/0031198 | A1 | 2/2021 | Tse Kwong et al. |
| 2021/0110545 | A1 | 4/2021 | Herold et al. |
| 2021/0181086 | A1 | 6/2021 | Chou et al. |

FOREIGN PATENT DOCUMENTS

| | | |
|---|---|---|
| JP | 2009511998 A | 3/2009 |
| KR | 100889617 B1 | 3/2009 |
| KR | 100889618 B1 | 3/2009 |
| KR | 100965222 B1 | 6/2010 |
| WO | 2004113908 A1 | 12/2004 |
| WO | 2007047761 A1 | 4/2007 |
| WO | 2009069418 A1 | 6/2009 |
| WO | 2012040067 A2 | 3/2012 |
| WO | 2014113110 A2 | 7/2014 |
| WO | 2018213721 A1 | 11/2018 |
| WO | 2020011487 A1 | 1/2020 |
| WO | 2021022050 A1 | 2/2021 |

OTHER PUBLICATIONS

Ellett, Felix, et al. "Diagnosis of sepsis from a drop of blood by measurement of spontaneous neutrophil motility in a microfluidic assay." Nature biomedical engineering 2.4 (2018): 207-214. (Year: 2018).*

"BD FACS Lyse Wash Assistant Streamline Sample Preparation Workflow", BD Biosciences, For In Vitro Diagnostics Use, downloaded from the internet Dec. 13, 2021.

"BD FACS™ Lyse Wash Assistant", BD Biosciences, https://www.bdbiosciences.com/en-us/products/instruments/sample-prep-systems/facs-lyse-wash-assistant, downloaded from the internet Dec. 13, 2021.

"Cytovale", https://cytovale.com, downloaded from the internet Dec. 13, 2021.

"Phantom v7.3, Phantom Camera Products", http://www.visionresearch.com/Products/, downloaded Feb. 16, 2022.

"TQ-Prep Workstation", Beckman Coulter Lifesciences, https://www.beckman.com/flow-cytometry/instruments/tq-prep, downloaded from the internet Dec. 13, 2021.

Guillou, Lionel, et al., "Development and validation of a cellular host response test as an early diagnostic for sepsis", PLOS ONE, Research Article, Apr. 15, 2021.

Natu, Rucha, et al., "Assessment of Flow through Microchannels for Inertia-Based Sorting: Steps toward Microfluidic Medical Devices", Micromachines, 2020, 11, 886, publishedSep. 24, 2020.

Bhagat, Ali Asgar, et al., "Intertial microfluidics for sheath-less high-throughput cytometry", Biomed. Microdevices 12(2), 187-195 (2010).

Bow, Hansen, "A microfabricated deformability-based flow cytometer with application to malaria", Lab Chip. Mar. 21, 2011; 11(6): 1065-1073. doi:10.1039/c0lc00472c.

Cha, Sukgyen, et al., "Cell Stretching Measurement Utilizing Viscoelastic Particle Focusing", Anal. Chem., 2012, 84, 10471-10477.

Chambers, Ann F., et al., "Metastasis: dissemination and growth of cancer cells in metastatic site", Nature Reviews cancer, vol. 2(8), p. 563-572, 2002.

Chen, J., et al., "Classification of cell types using a microfluidic device for mechanical and electrical measurement on single cells", Lab Chip, 2011, 11, 3174-3181.

Choi, Sungyoung, et al., "Sheathless hydrophoretic particle focusing in a microchannel with exponentially increasing obstacle arrays", Anal Chem., 80(8):3035-9 (2008).

Crawford, Katherine, et al., "Rapid Biophysical Analysis of Host Immune Cell Variations Associated with Sepsis", American Journal of Respiratory and Critical Care Medicine, vol. 198, No. 2, Jul. 15, 2018.

Cross, Sarah E, et al., "Nanomechanical analysis of cells from cancer patients", Nat Nano 2:780-783 (2007).

Di Carlo, Dino, et al., "Continuous inertial focusing, ordering, and separation of particles in microchannels", Proc Natl Acad Sci USA 104:18892-18897 (2007).

Di Carlo, Dino, et al., "Dynamic Single-Cell Analysis for Quantitative Biology", Analytical Chemistry 78:7918-7925 (2006).

Di Carlo, Dino, "Inertial microfluidics", Lab Chip 9:3038-3046 (2009)., Oct. 31, 2017 00:00:00.0.

(56) References Cited

OTHER PUBLICATIONS

Di Carlo, Dino , et al., "Particle Segregation and Dynamics in Confined Flows", Phys. Rev. Lett. 102 (2009).
Dobbe, J.G.G , et al., "Measurement of the Distribution of Red Blood Cell Deformability Using an Automated Rheoscope", Cytometry (Clinical Cytometry), vol. 50, pp. 313-325, 2002., Oct. 31, 2017 00:00:00.0.
Dudani, Jaideep S., et al., "Pinched-flow hydrodynamic stretching of single-cells+", Lab Chip, 2013, 13, 3728.
Dylla-Spears, Rebecca , et al., "Single-molecule detection via microfluidic planar extensional flow at a stagnation point", Lab on a Chip, vol. 10, pp. 1543-1549, Mar. 2010., Oct. 31, 2017 00:00:00. 0.
Fardi, Muhammad Asim , et al., "Elasto-inertial microfluidics for bacteria separation from whole bloods for sepsis diagnostics", Journal of Nanobiotechnology, (2017) 15:3.
Fregin, Bob , et al., "High-throughput single-cell rheology in complex samples by dynamic real-time deformability cytometry", Nature Communications, (2019)10:415.
Gossett, D.R. , et al., "Deformability Cytometry: High-Throughput, Continuous Measurement of Cell Mechanical Properties in Extensional Flow", 14th International Conference on Miniaturized Systems for Chemistry and Life Sciences Oct. 3-7, 2010, Groningen, The Netherlands.
Gossett, Daniel R., et al., "Hydrodynamic stretching of single cells for large population mechanical phenotyping", 7630-7635, PNAS, May 15, 2012, vol. 1091, No. 20.
Gossett, Daniel R., et al., "Leukocyte Mechanophenotyping by Deformability Cytometry", 16th International Conference on Miniaturized Systems for Chemistry and Life Sciences Oct. 28-Nov. 1, 2012, Okinawa, Japan {3pages).
Gossett, Daniel R., et al., "Particle focusing mechanisms in curving confined flows", Anal Chem 81 :8459-8465,2009.
Guck, J. , et al., "Optical Deformability as an Inherent Cell Marker for Testing Malignant Transformation and Metastatic Competence", Biophysical Journal, vol. 88, May 2005, 3689-3698.
Gunsolus, Ian L., et al., "Diagnosing and Managing Sepsis by Probing the Host Response to Infection: Advances, Opportunities, and Challenges", Journal of Clinical Microbiology, vol. 57, Issue 7, Jul. 2019.
Guo, Q. , "Microfluidic Device for Measuring the Deformability of Single Cells", Doctorate Thesis, The University of British Columbia, Apr. 2012, 1-24 (total 78 pages., Oct. 31, 2017 00:00:00.0.
Lee, Won Hee , et al., "Dynamic self-assembly and control of microfluidic particle crystals", Proc. Natl. Acad. Sci. U.S.A, 107, 22413-22418 (2010).
Lincoln, Bryan , et al., "Deformabilily-Based Flow Cytometry", Cytometry Part A, vol. 59A, pp. 203-209, 2004.
Mao, Xiaole , et al., "Single-layer planar on-chip flow cytometer using microfluidic drifting based three-dimensional (3D) hydrodynamic focusing", Lab Chip, 9, 1583-1589 (2009).
Mutlu, Baris R., et al., "Oscillatory inertial focusing in infinite microchannels", PNAS, vol. 115, No. 30, 7682-7687, Jul. 24, 2018.
Oakey, John , et al., "Particle Focusing in Staged Inertial Microfluidic Devices for Flow Cytometry", Anal. Chem., 82, 3862-3867 (2010)., Oct. 31, 2017 00:00:00.0.
Oeschger, Taylor , et al., "Point of care technologies for sepsis diagnosis and treatment", Lab Chip, 2019, 19, 728-737.
Park, Jae-Sung , et al., "Continuous focusing of microparticles using intertial lift force and vorticity via multi-0rifice microfluidic channels", Lab on a Chip, 9, 939-48 (2009).
Perkins, Thomas T, et al., "Single Polymer Dynamics in an Elongational Flow", Science 276:2016-2021 (1997)., Oct. 31, 2017 00:00:00.0.
Sawetzki, Tobias , et al., "Viscoelasticity as a Biomarker for High-Throughput Flow Cytometry", Biophysical Journal, vol. 105, Nov. 2013, pp. 2281-2288.

Shelby, Patrick J, et al., "A microfluidic model for single-cell capillary obstruction by Plasmodium falciparum-infected erythrocytes", PNAS, vol. 100, pp. 14618-14622, 2003.
Squires, Todd , et al., "Microfluidics: Fluid physics at the nanoliter scale", Rev. of Modern Physics, vol. 77, pp. 977-1026, 2005., Oct. 31, 2017 00:00:00.0.
Sraj, Ihab , et al., "Cell deformation cytometry using diode-bar optical stretchers", J Biomed Opt 15 (2010).
Suresh, S. , et al., "Connections between single-cell biomechanics and human disease states: gastrointestinal cancer and malaria.", Acta Biomater 1:15-30 (2005).
Thery, Manuel , et al., "Get round and stiff for mitosis", HFSP J 2:65-71 (2008).
Tse, Henry T.K., et al., "Quantitative Diagnosis of Malignant Pleural Effusions by Single-Cell Mechanophenotyping", Science Translational Medicine, Nov. 20, 2013: vol. 5, Issue 212, pp. 212ra163.
Yamada, Masumi , et al., "Hydrodynamic filtration for on-chip particle concentration and classification utilizing microfluidics", Lab Chip, 5, 1233-1239 (2005)., Oct. 31, 2017 00:00:00.0.
Yap, Belinda , et al., "Cystoskeletal remodeling and cellular activation during deformation of neutrophils into narrow channels", J. Appl. Physiol, vol. 99, pp. 2323-2330, 2005.
Young, Susan M, et al., "High-Throughput Microfluidic Mixing and Multiparametric Cell Sorting for Bioactive Compound Screening", J. Biomol Scree, vol. 9, pp. 103-111, 2004., Oct. 31, 2017 00:00:00. 0.
Zheng, Bo , et al., "Formation of Droplets of Alternating Composition in Microfluidic Channels and Applications to Indexing of Concentrations in Droplet-Based Assays", Anal. Chem., vol. 76, pp. 4977-4982, 2004.
Minamitani, Haruyuki , et al., "Deformability Cytometry: High-Throughput, Continuous Measurement of Cell Mechanical Properties in Extensional Flow", BMES/EMBS Conference, 1999, Proceedings of the First Joint Atlanta, GA, USA Oct. 13-16, 1999, Piscataway, NJ, USA, IEEE, US, vol. 1, Oct. 13, 1999 (Oct. 13, 1999_, p. 72, XPO10357477, DoI: 10.1109/IEMBS. 1999.802107, ISBN: 978-0-7803-5674-0.
Jalali, Bahram , et al., "Evolution of Photonic Time Stretch: From Analog to Digital Conversion to Blood Screening", arXiv:1106. 5518 physics.ins-det, Submitted Jun. 27, 2011.
Gossett, Daniel R., et al., "Label-free cell separation and sorting in microfluidic systems", Apr. 25, 2010, Springer, Anal. Bioanal. Chem., 397, pp. 3249-3267.
Morton, K.J. , et al., "Crossing microfluidic streamlines to lyse, label and wash cells", Lab Chip 8, 1448-1453 (2008).
Petersson, F. , et al., "Carrier Medium Exchange through Ultrasonic Particle Switching in Microfluidic Channels", Anal. Chem. 77, 1216-1221 (2005).
Tornay, R. , et al., "Dielectrophoresis-based particle exchanger for the manipulation and surface functionalization of particles", Lab Chip 8, 267-273 (2008).
Yamada, M. , et al., "Millisecond treatment of cells using microfluidic devices via two-step carrier medium exchange", Lab Chip, 8, 772-778 (2008).
Zhang, Xunil , et al., "Continuous flow separation of particles within an asymmetric microfluidic device", 2006, RSC, :ab Chip, 6, 561-566.
Zhang, J. , et al., "Inertial focusing in a straight channel with asymmetrical expansion-contraction cavity arrays using two secondary flows", J. Micromech. Microeng. 23 (2013) 08023 (13pp).
Issekutz, Andrew C., "Role of ICAM-1 and ICAM-2 and alternate CD11/CD18 ligands in neutrophil transendothelial migration", 1999, 65, 117-126 (Year 199).

\* cited by examiner

SYSTEM AND METHOD FOR IMMUNE ACTIVITY DETERMINATION

CROSS-REFERENCE TO RELATED APPLICATIONS

This application is a continuation of U.S. application Ser. No. 16/943,716, filed 30 Jul. 2020, which claims the benefit of U.S. Provisional Application No. 62/881,283, filed 31 Jul. 2019, which is incorporated in its entirety by this reference. This application is related to U.S. application Ser. No. 16/374,663 filed 3 Apr. 2019 and entitled 'SYSTEM AND METHOD FOR DEFORMING AND ANALYZING PARTICLES,' U.S. application Ser. No. 15/868,025 filed 11 Jan. 2018 entitled 'METHOD AND DEVICE FOR HIGH THROUGHPUT CELL DEFORMABILITY MEASUREMENTS,' and U.S. application Ser. No. 16/676,352 filed 6 Nov. 2019 and entitled 'METHOD AND DEVICE FOR HIGH-THROUGHPUT SOLUTION EXCHANGE FOR CELL AND PARTICLE SUSPENSIONS' each of which is incorporated in its entirety by this reference.

STATEMENT OF GOVERNMENT SUPPORT

This invention was made with government support under National Science Foundation grants IIP-1315895 and IIP-1431033. The government has certain rights in the invention.

TECHNICAL FIELD

This invention relates generally to the health field, and more specifically to a new and useful system and method in the health field.

BACKGROUND

The innate immune system acts as a first line of defense with its cellular components rapidly activating in response to danger signals. Circulating innate immune cells, such as neutrophils and monocytes, react to these signals by changing their phenotypes to fulfill numerous roles. These changes allow categorization of the innate immune cells into subpopulations that are functionally diverse.

Neutrophil activation leads to changes in migration, secretion, and function that are critical in resolving infections; however, aberrant activation can also result in a number of pathologies, including the life threatening, dysregulated host immune response to infection known as sepsis. Beyond well-known phagocytic and cytotoxic secretory functions, neutrophils responding to danger signals adopt chemotactic behaviors, secrete a host of cytokines to direct other immune function, and extrude fibrillar networks of DNA and antimicrobial proteins—termed neutrophil extracellular traps (NETs).[3] While NET formation appears to have a physiological role in trapping and killing bacteria in local infections, it is also implicated in the pathobiology of sepsis as well as certain autoimmune diseases, such as systemic lupus erythematosus and small vessel vasculitis. Taking into account these links with disease, the ability to quantify the degree of innate immune activation can aid with the diagnosis, prognosis or monitoring of a wide variety of disorders.

A number of approaches have been developed to quantify neutrophil activation; however, many of these techniques are either too slow or too specialized to be used in clinical settings. Thus, there is a need in the health field to create a new and useful system and method. This invention provides such a new and useful system and method.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Overview.

Figure 2:
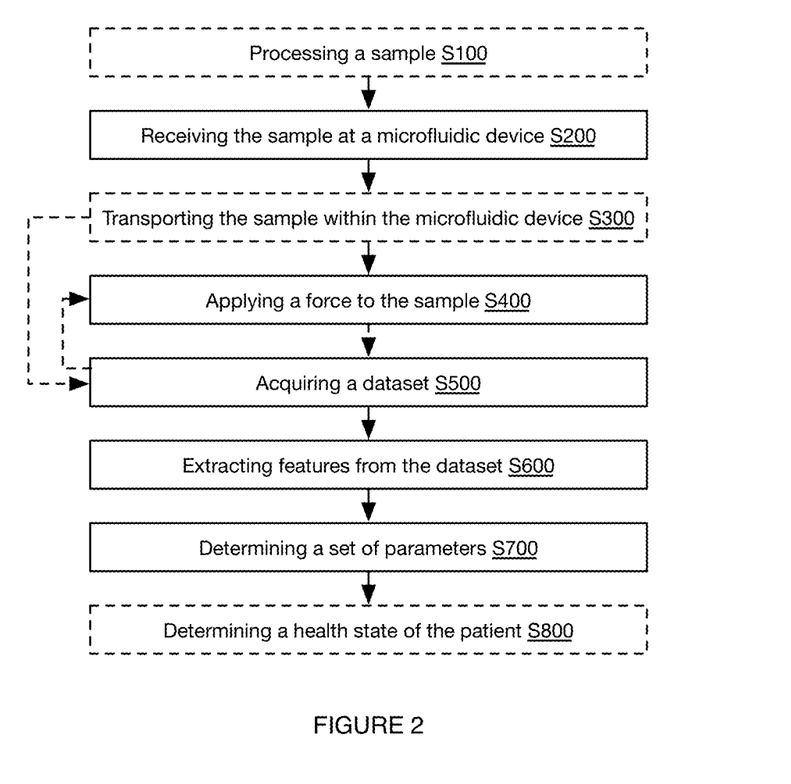
FIG. 2 is a schematic representation of the method.

As shown in FIG. 2, the method can include receiving a sample at a microfluidic device, applying a stress to the sample, acquiring a dataset associated with the sample, extracting features from the dataset, determining parameters based on the extracted features. The method can optionally include processing the sample, transporting the sample within a microfluidic device, determining a health state of the patient, and/or any steps.

Figure 1:
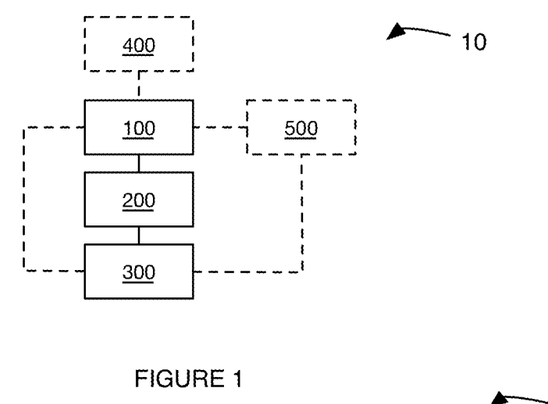
FIG. 1 is a schematic representation of the cytometry system.

As shown in FIG. 1, the cytometry system 10 can include a microfluidic device 100, a detection system 200, and a computing system 300. The cytometry system can optionally include a temperature controller 500, a sample preparation module 400, and/or any suitable component.

The system and method are preferably used to measure and detect biophysical properties of cells, but can measure properties of any particle and/or material (e.g., that fits in the microfluidic channels). The system and/or method can additionally or alternatively function to diagnose a health state of the patient. In a specific example, the system and/or method can be used in an emergency department (e.g., of a hospital), urgent care, and/or doctor's office to triage patients (e.g., diagnoses and/or determined probability that a patient is experiencing a condition such as a sepsis-related condition). However, the system and/or method can be used in any manner.

In a specific example, the method can include providing a blood sample (e.g., a plurality of white blood cells, a plurality of blood cells, etc.) to the microfluidic device, focusing (and aligning) the plurality of blood cells into a first channel of the microfluidic device, applying a (noncontact) stress to each blood cell (e.g., individually applying the stress to each blood cell) of the plurality of blood cells at an deformation region of the microfluidic device (e.g., by applying a hydrodynamic force to the plurality of blood cells by intersecting a second channel including fluid with blood cells from the first channel), acquiring an optical dataset before, during, and after stress has been applied to the blood cell, and determining a cell parameter based on the optical dataset. In this specific example, the cell parameter can be associated with a cell shape, a cell count, biophysical parameters, and/or include a trajectory parameter of the cell (e.g., based on a characteristic of a trajectory of the cell such as an oscillation of the centroid of the cell). In this specific example, the method can further include determining an index using the cell parameters and a model (e.g., a logistic regression), and determining an immune activation state of the patient when the index exceeds a threshold.

2. Benefits.

Variations of the technology can confer several benefits and/or advantages.

First, the inventors have discovered that including trajectory parameters (e.g., alternatively or in addition to enumeration parameters, morphological parameters, etc.) can enhance (e.g., increase accuracy, increase specificity, increase speed, enable, etc.) the determination of an immune activation state (e.g., sepsis-related condition) of a patient. The trajectory parameters can provide (complementary) information regarding the mechanical properties of the cells, thereby enhancing the determination of the immune activation state of a patient.

Second, variants of the technology can rapidly (e.g., <1 min, <2 min, <5 min, <10 min, <20 min, <1 hour, etc.) determine (e.g., diagnose) the immune activation state (e.g., high/medium/low activation; septic or not septic; etc.) of the patient. In specific examples, reproducibility can be ensured by: using a flow (e.g., in the deformation region) with a Reynolds number at least 100 (e.g., 100, 150, 200, 300, 500, 1000, 1500, 2000, 2500, 3000, 10000, 100-3000, etc.), by maintaining the temperature of the microfluidic device (and/or sample and sheath fluid) within a predetermined range, by considering a subset of the peaks of oscillations in the trajectory to determine the trajectory parameter (e.g., by excluding the first peak, by excluding the first and second peak, by excluding the first cycle, by excluding the second cycle, etc.; by using the third peak, by using the third, fourth, and fifth peak, by using a ternary cycle, by using quaternary cycle, by using quintenary cycle, by using peaks after and/or including the third oscillation peak, etc.; etc.), and/or in any manner. By reproducibly analyzing a large number of cells (e.g., greater than about 1000; 10000; 20000; 50000; 100000; 500000; 1000000; etc.), these specific examples can rapidly and accurately determine the immune activation state of the patient.

Third, variants of the technology can determine a set of parameters that can be correlated to one or more health and/or disease states of a patient. In specific examples, by acquiring images with a high rate camera, a plurality of images of the sample before, during, and after experiencing stress can be measured, which can enable one or more structural and/or trajectory parameters to be determined.

However, variants of the technology can confer any other suitable benefits and/or advantages.

3. Cytometry System.

As shown in FIG. 1, the cytometry system 10 can include a microfluidic device 100, a detection system 200, and a computing system 300. The cytometry system can optionally include a temperature controller 500, a sample preparation module 400, and/or any suitable component.

The microfluidic device preferably functions to receive a sample, sort (e.g., align, focus, separate, etc.) one or more constituents (e.g., cells) of a sample, and apply a force (e.g., stress, strain, etc.) to the sample and/or constituents thereof in a deformation region. The microfluidic device preferably applies a contactless force (e.g., hydrodynamic force) to the constituents, but can additionally or alternatively apply a contact force (e.g., using pores, micropipettes, cantilevers, etc.) to the constituents. In a specific example, the microfluidic device does not apply a contact force to deform the constituents for analysis. The microfluidic device can deform the: entire constituent, constituent components (e.g., cell nuclei, cell cytoskeleton, etc.), and/or other portions of the constituent. The microfluidic device is preferably capable of processing thousands of constituents a second in series and/or in parallel, but can alternatively process more or less cells. The force deformation and/or analysis is preferably non-destructive (e.g., such that the cells can be subsequently used in secondary analyses), but can alternatively be destructive (e.g., lyse the cells, etc.).

The sample preferably includes a plurality of cells (e.g., blood cells, bacteria, etc.), but can include any particles or constituents that fit within the microfluidic channel. The sample is preferably suspended in sheath fluid, but can be suspended in any fluid, used as received (e.g., using blood serum as the fluid, using blood plasma as the fluid, etc.), and/or otherwise be provided. The sample is preferably extracted from peripheral blood (e.g., whole blood), but can be venous blood, bone marrow, and/or another biological sample. The sample can be associated with auxiliary information, such as patient information; sample parameters; treatment parameters; collection parameters; and/or other data. The auxiliary information can be used to interpret the index (e.g., select different index calculations or scales for interpretation), determine secondary analyses, determine treatment parameter recommendations, and/or otherwise used.

The cell parameters determined using the device can be related to: mechanical properties (e.g., deformability, stress-strain relation, young's modulus, etc.), time-varying properties (e.g., velocity, trajectory, visco-elastic inertial response (VEIR), deformability, oscillation frequency, oscillation amplitude, deviation of the particle flow trajectory, residence time, etc.), numerosity (e.g., number of constituents, number of constituents per unit volume, number of a specific type of constituent, relative amount of one constituent to another, etc.), constituent type (e.g., type of cells, cell classification, cell population, cell subpopulation, etc.), constituent density, constituent state (e.g., cell life cycle phase, state of cell nucleus, etc.), activation properties (e.g., immunofluorescence rate, intensity, etc.), and/or any property. In specific examples, the microfluidic device can be configured and/or arranged for constriction-based deformability cytometry (cDC), shear flow deformability cytometry (sDC), and/or extensional flow deformability cytometry (xDC). However, the microfluidic device can be arranged in any manner.

The Reynold's number of the sample and/or sheath fluid within the microfluidic device (and/or region of the microfluidic device) is preferably between about 1-3000 such as 1, 5, 10, 20, 50, 70, 75, 100, 150, 200, 300, 500, 1000, 1500, 2000, or 2500. However, the Reynold's number can be less than 1 or greater than 3000. The Reynold's number can be substantially constant (e.g., vary by less than about 5%, 10%, 20%, 30%, etc.) within the microfluidic device and/or variable (e.g., vary by greater than 30%) within the microfluidic device (e.g., different Reynold's number in different regions of the device).

Figure 3:
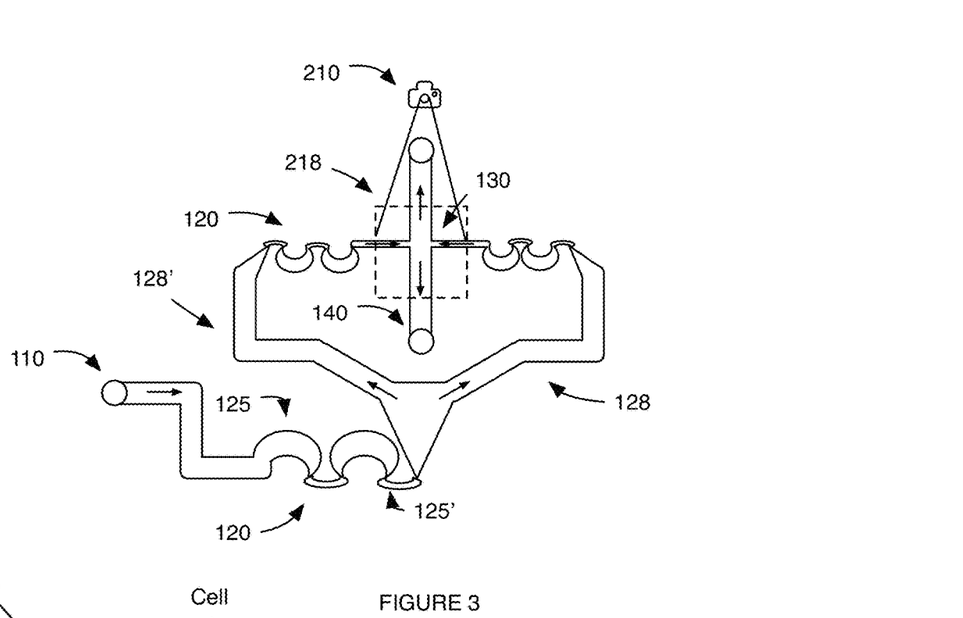
FIG. 3 is a schematic representation of an example of a microfluidic channel.

In a specific example, as shown in FIG. 3, the microfluidic device can include an inlet 110, a focusing region 120, a deformation region 130, and an outlet 140. However, the microfluidic device can include any suitable regions and/or components.

The inlet functions to receive the sample. The inlet is preferably arranged upstream of the focusing region, but can be arranged downstream of the focusing region and/or at any suitable location. In some variations, the microfluidic device can include a plurality of inlets. In these variations each inlet can receive the same sample(s) and/or different samples. In an illustrative example, one inlet can receive a blood sample and a second inlet can receive sheath fluid. In a second illustrative example, one inlet can receive a blood sample and a second inlet can receive a control sample (e.g., constituents with known properties).

The focusing region functions to focus and align the constituents of the sample. The focusing region can additionally or alternatively function to ensure that the sample (and/or constituent thereof) enters the deformation region in a predetermined manner. In specific examples, the predetermined manner can be a single constituent (e.g., cell) in the deformation region at a time, a predetermined time between constituents entering the deformation region, constituents entering the deformation region from a particular direction, constituents entering the deformation region with threshold and/or target kinematics (e.g., speed, velocity, acceleration, etc.), and/or be in any manner. The focusing region is preferably upstream of the deformation region, but can be downstream of and/or collocated with the deformation region.

The focusing region is preferably an inertial focusing region, but a noninertial focusing region, forced focusing region (e.g., using pumps, gating, etc.) or any suitable focusing region can be used. The focusing region preferably uses asymmetric channels 125 125', but can use symmetric channels. In a specific example, the focusing region is serpentine, with alternating regions of small radius of curvature and larger radius of curvature. In a second specific example, the focusing region is serpentine with alternating regions of wider channels and narrow channels. However, the focusing region can be a zigzag channel, square channels, serpentine channels (e.g., with substantially constant width, with substantially constant radii of curvature, etc.), hairpin channels, and/or any suitable channel morphology.

The sample can exit the focusing region into the deformation region, an outlet, an inlet, a channel, and/or to any suitable region. The sample preferably exits the focusing region into a single channel 128 (e.g., greater than 75%, 80%, 85%, 90%, 95%, 99%, 99.99%, etc. of the constituents of the sample are directed into the single channel). However, the sample can exit the focusing region into a plurality of channels (e.g., a different channel for different cell types, a different channel for different cell sizes, more than one channel that the sample can enter, etc.), and/or the sample can be provided to any suitable channel(s) after the focusing region. The sheath fluid is preferably provided to a plurality of channels 128 128'(e.g., split approximately evenly between the plurality of channels such as approximately 50/50 for two channels; split unevenly between the plurality of channels such as 95/5, 90/10, 80/20, 70/30, 60/40, etc. for two channels; etc.) at the output of the focusing region, but can be provided to a single channel or to any suitable channel(s) with any flow properties.

In variants, the microfluidic device can include a plurality of focusing regions. The focusing regions can arranged in series and/or in parallel. Each focusing region can be the same or different from other focusing regions.

The deformation region functions to apply a force (e.g., stress) to the sample, for example, by utilizing a change in velocity. The deformation region preferably applies the force to individual constituents of the sample at a time (e.g., stress is applied to a single cell as the cell passes through the deformation region), but can apply the force to a subset of (and/or the entire) sample simultaneously. The force is preferably a noncontact force (e.g., a hydrodynamic force), but can be a contact force. The force is preferably sufficiently large to induce a deformation in the sample (and/or constituents thereof) without damaging the sample. However, the force can damage the sample (e.g., lyse one or more cells), perturb the sample, redirect one or more flow properties of the sample, not deform the sample, and/or otherwise influence the sample. The deformation region is preferably upstream of one or more outlets, but can be downstream or and/or collocated with the outlet(s).

The blood sample preferably changes direction as it passes through the deformation region. However, the blood sample can continue in the same direction. In an illustrative example, the blood sample can exit the deformation region orthogonal to the direction that the blood sample enters. However, the blood sample can leave the deformation region at any angle between 0-180° relative to the direction that the blood sample enters the deformation region. For example, the deformation region can include an L-shaped channel, a T-shaped channel, a boustrophedonic or serpentine channel, an extensional flow region, expansion channels, contraction channels, as shown in FIGS. 10A-10D, and/or any suitable geometry(s).

The deformation region preferably applies the force to the blood sample by changing the velocity of the cells (and/or fluid). The velocity of the cells can be reduced and/or increased. The velocity is preferably changed by at least about 10% (e.g., 15%, 20%, 25%, 30%, 35%, 40%, 50%, 60%, 75%, 80%, 90%, 100%, 200%, 500%, 15-100%, etc.), but can be changed by less than 30%. The change in velocity can be provisioned by a geometry of the deformation region, an intersection of two or more flow channels, and/or in any manner. However, the force can be otherwise applied.

Figure 7:
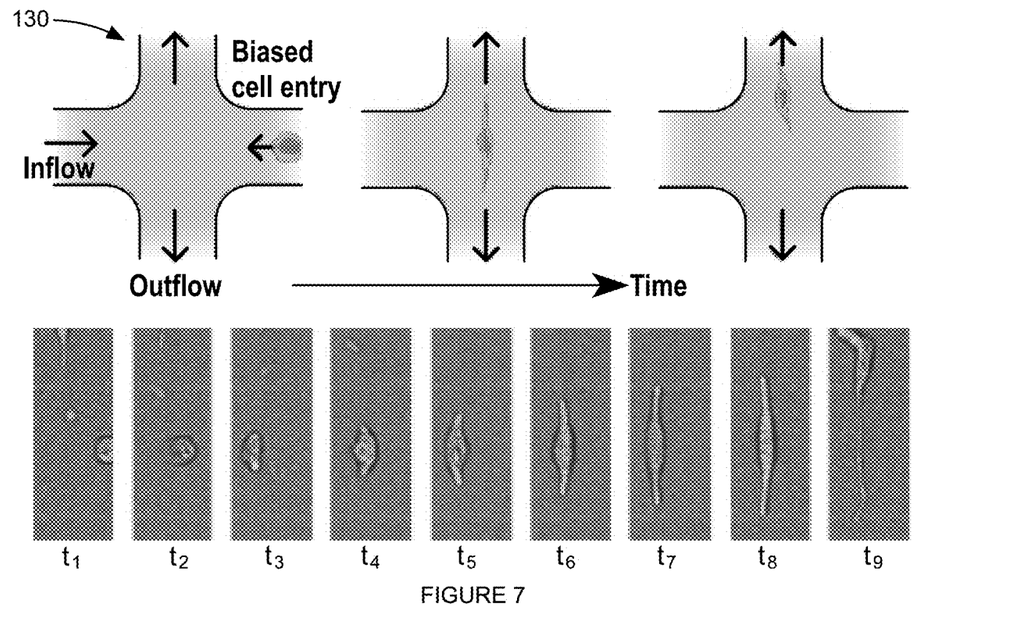
FIG. 7 is a cartoon representation of an example of applying a force to a cell in a deformation region of a microfluidic device and example images of a cell within the deformation region.

In a specific example, as shown in FIG. 7, the force can be generated by crossing two or more channels (e.g., fluid flow paths). The flow paths are preferably antiparallel (e.g., arranged such that fluid exits one channel in a first direction and another channel in the opposite direction, where the force is greatest in the intersection region of the fluid paths), but can be parallel (e.g., to generate a strain on the sample), perpendicular, and/or intersect at any angle(s). The flow paths are preferably offset from one another by an offset distance. The offset distance can function to induce a vorticity in the fluid (and/or sample) within the deformation region and/or to provide an asymmetric force to the sample. The offset distance can depend on the sample, be predetermined (e.g., an offset or range thereof between 0.1-20 μm such as 1 μm, 2 μm, 5 μm, 10 μm, etc.), and/or be otherwise determined. However, the flow paths can be substantially aligned (e.g., offset distance less than 0.1 μm) and/or otherwise arranged. Alternatively, the force can be generated by the same fluid in the same fluid flow path (e.g., by changing flow directions).

The outlet(s) function to enable sample to be removed from the microfluidic device without clogging. In a specific example, the microfluidic device can include two outlets arranged perpendicular to a pair of fluid flows that make-up the deformation region. However, the outlets can be arranged in any manner.

In some variants, the microfluidic device can be arranged as and/or include components or regions of microfluidic devices as described in U.S. application Ser. No. 16/374,663 filed 3 Apr. 2019 and entitled 'SYSTEM AND METHOD FOR DEFORMING AND ANALYZING PARTICLES,' U.S. application Ser. No. 15/868,025 filed 11 Jan. 2018 entitled 'METHOD AND DEVICE FOR HIGH THROUGHPUT CELL DEFORMABILITY MEASUREMENTS,' and/or U.S. application Ser. No. 16/676,352 filed 6 Nov. 2019 and entitled 'METHOD AND DEVICE FOR HIGH-THROUGHPUT SOLUTION EXCHANGE FOR CELL AND PARTICLE SUSPENSIONS' each of which is incorporated in its entirety by this reference.

The microfluidic device can include and/or be coupled to a flow device, which functions to generate a fluid flow within the microfluidic device. The flow device can include a pump, an impeller, and/or any other flow device. The flow device can provide a negative and/or positive pressure (e.g., push fluid through, pull fluid through, etc. the microfluidic channel).

However, the microfluidic device can be arranged in any manner.

The computing system can function to process one or more datasets (e.g., determine features of the sample, determine a set of parameters associated with the sample, etc.), diagnose a health state of the patient, generate a model for diagnosing the health state of the patient, and/or perform any function. The computing system can be local (e.g., to the sample preparation module, to the detection system, to the microfluidic device, etc.), remote (e.g., a server, cloud computing, etc.), and/or distributed. The computing system is preferably communicably coupled to the detection system, but can additionally or alternatively be communicably coupled to the microfluidic device, the sample preparation module, and/or any suitable component.

The detection system functions to generate a dataset associated with the sample. The dataset is preferably associated with the sample (and/or constituents thereof) proximal the deformation region, but can be associated with the sample proximal the focusing region, the inlet, the outlet, in the sample preparation module, and/or other sample location. The dataset is preferably a plurality of images 210 of each component of the sample (e.g., a plurality of images of each cell), but can be an electrical dataset, a force dataset (e.g., a contact force), a flow dataset (e.g., measuring a change of the flow when a constituent of the sample is proximal to and/or in the deformation region), a thermal dataset, and/or any other dataset. The plurality of images of a constituent preferably includes at least 10 images of the constituent, but can include less than 10 images. The plurality of images preferably includes images of the constituent before, during, and after applying the force to the constituent. However, the plurality of images can correspond to images of the constituent before force application, before and during force application, before and after force application, during force application, during and after force application, after force application, and/or any suitable timing.

The detection system 200 is preferably an image acquisition system 210 such as a microscope (e.g., an inverted microscope, an upright microscope, etc. such as configured to acquire bright-field images, dark-field images, fluorescent images, etc. of the sample), a camera 212, and/or any image acquisition system. Images 215 are preferably acquired at a frame rate that is at least 100,000 frames per second such as 200,000; 300,000; 500,000; 750,000; 1,000,000; 2,000,000; 5,000,000; 10,000,000 frames per second, etc. However, images can be acquired at less than 100,000 frames per second and/or at any rate. The field of view 218 of the image acquisition system is preferably centered on a stagnation point 135 (e.g., a point where the flow paths and/or forces are balanced) of the deformation region. However, the stagnation point can be aligned to an edge, a corner, arbitrarily, a predetermined location, randomly, and/or otherwise aligned relative to the image acquisition system (e.g., within the captured images). However, the image acquisition system can be otherwise arranged.

The microfluidic device can optionally include one or more alignment guide proximal the deformation region. The alignment guide(s) function to enable image calibration and/or microfluidic device alignment.

The sample preparation device functions to prepare a sample to be introduced into the microfluidic device. The sample preparation device can remove one or more constituent of the sample, dilute and/or concentrate the sample to a predetermined concentration, perform a solvent and/or buffer exchange, adjust a sample property (e.g., temperature, pH, viscosity, ionic strength, etc.), and/or otherwise prepare the sample. In an illustrative example, the sample preparation device can separate red blood cells (and/or platelets) from white blood cells (leukocytes). In a first variation of this example, the sample preparation device can lyse the red blood cells (e.g., using a red blood cell lysis buffer such as including ammonium chloride, potassium carbonate, EDTA, formic acid, etc.). In a second variation of this example, a white blood cells can be separated from red blood cells (e.g., using flow sorting, centrifugation, sedimentation, etc.). However, the sample can be prepared in any manner.

The optional temperature regulator functions to maintain the temperature of the microfluidic device within a predetermined temperature range, which can help improve the reliability and/or reproducibility of the measurements. The temperature is preferably maintained within ±20° C. of a target set temperature such as within 0.1° C., 0.5° C., 1° C., 2° C., 5° C., 10° C. However, the temperature can be maintained within an asymmetric range of the target temperature, and/or can be maintained within any range of the target temperature. The target temperature is preferably between 17-41° C. such as 20° C., 22° C., 25° C., 30° C., 35° C., 37° C., 38° C., or 40° C. However, the target temperature can be an y temperature. The temperature regulator preferably includes active feedback control (e.g., a PID controller, a PI controller, etc.). The temperature regulator can include a heater (e.g., an IR heater, a resistive heater, etc.) and/or a cooler (e.g., refrigeration, thermoelectric cooler, heat sink, etc.).

However, the cytometry system can include any components.

4. Method.

Figure 9:
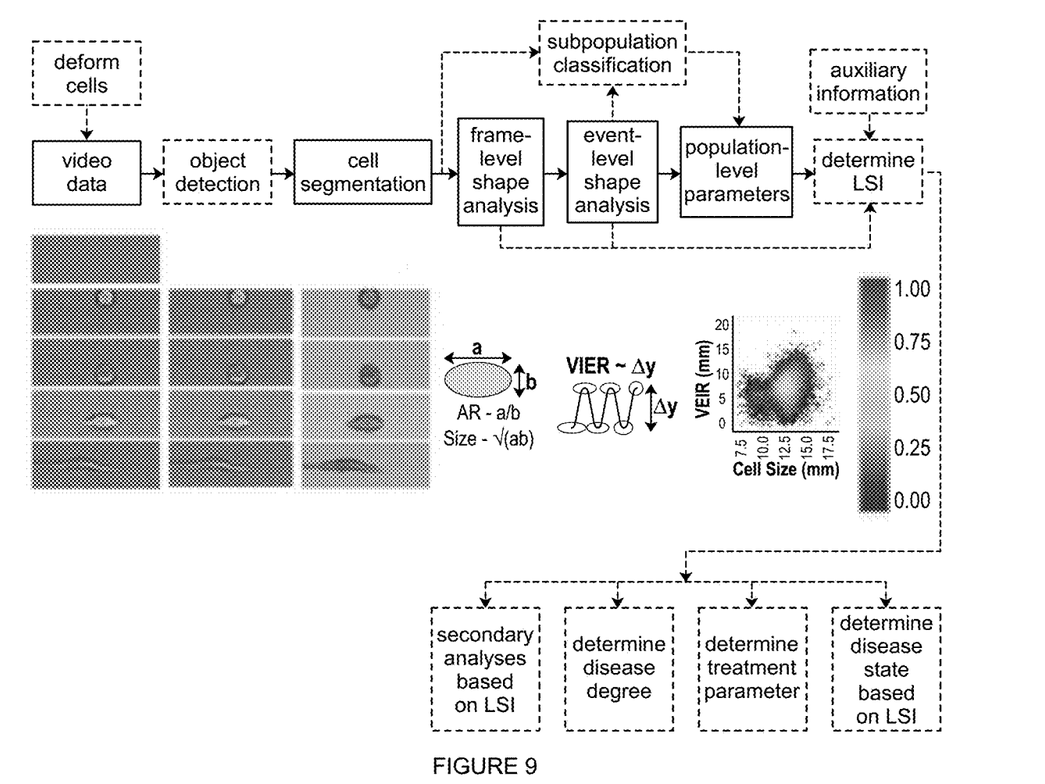
FIG. 9 is a schematic representation of an example of the method.
Figures 10A, 10B:
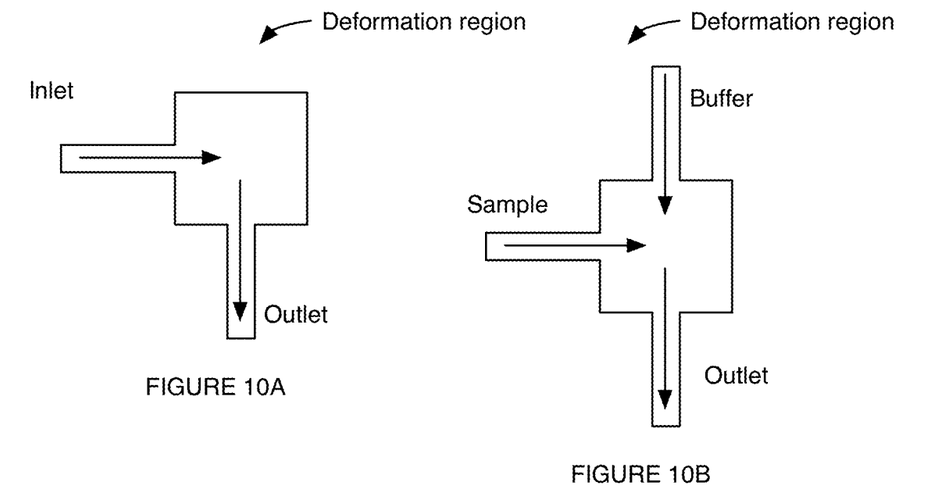
FIGS. 10A-10D are schematic representations of examples of deformation region geometries.
Figure 10C:
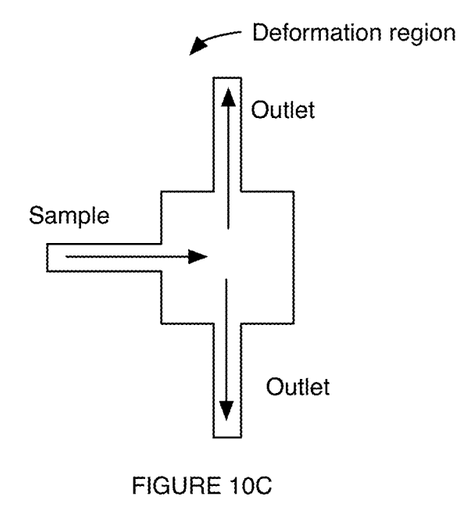
Figure 10D:
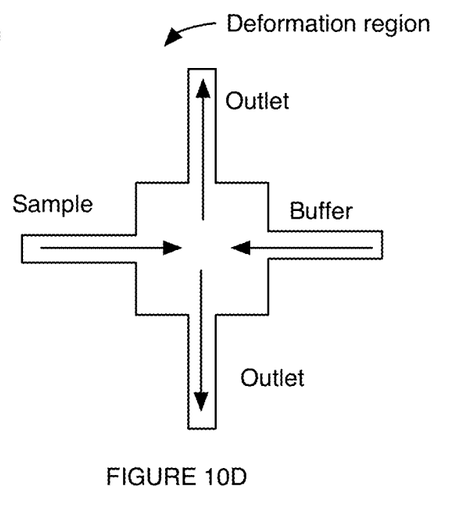

As shown in FIG. 2, the method can include receiving a sample at a microfluidic device, applying a stress to the sample, acquiring a dataset associated with the sample, extracting features from the dataset, determining parameters based on the extracted features. The method can optionally include processing the sample, transporting the sample within a microfluidic device, determining a health state of the patient, and/or any steps. A specific example is shown in FIG. 9.

The method is preferably performed by a microfluidic system, (e.g., as described above, such as a cytometry system), but can be performed by any system. The method can be performed in real- or near-real time (e.g., during microfluidic device operation, during cell deformation), but can be performed asynchronously or at any other suitable time.

Processing the sample S100 functions to prepare the sample for measurements. In one example, processing the sample functions to isolate the leukocytes from the blood sample. In a second example, processing the sample functions to isolate individual leukocyte subpopulations (e.g., monocytes, lymphocytes, neutrophils, etc.). However, the sample can be processed for any other suitable purpose. Processing the sample is preferably performed by a sample preparation device but can be performed by any component. Examples of processing the sample can include separating one constituent type from another (e.g., separating white blood cells (leukocytes) from red blood cells (erythrocytes); separating cell subpopulations or specific cell type such as such as monocytes, lymphocytes, neutrophils, eosinophils, basophils, macrophages, erythrocytes, platelets, bacteria, viruses, fungi, combinations thereof; etc.), lysing one or more constituents (e.g., lysing red blood cells), performing a solvent and/or buffer exchange, adjusting a sample property (e.g., temperature, pH, viscosity, ionic strength, concentration, etc.), and/or can otherwise process the sample. However, the sample can be processed in any manner. In an illustrative example, lysing red blood cells from the blood sample can include lysing red blood cells using formic acid (e.g., a formic acid lysis system). In this illustrative example, the lysis mixture can be centrifuged (e.g., at 100, 200, 300, 400, 500, 600, 700, 800, 900, 1000, 2000, 5000, 10000, etc. G) for a predetermined amount of time (e.g., 1 s, 5 s, 10 s, 30 s, 1 min, 2 min, 5 min, 10 min, 20 min, 30 min, etc.) and the supernatant (and/or precipitate) discarded. However, red blood cells can additionally or alternatively be lysed in any manner.

Receiving a sample S200 functions to provide the sample to a microfluidic device. The sample is preferably a blood sample (e.g., a plurality of blood cells, a plurality of white blood cells, a plurality of red blood cells, etc. of a patient, user, subject, member of a test group, control, animal, etc.). However, the sample can additionally or alternatively include any suitable cells, particles, and/or other constituents. In some variations, the sample can include a plurality of control particles. The control particles can function to monitor flow characteristics of the microfluidic device. The control particles can include: beads (e.g., polystyrene beads), crystals, and/or any suitable control particle. The control particles preferably have a size comparable to the sample (e.g., ±50%, ±100%, etc. of the size of the sample constituents), but can have a predetermined size (e.g., based on the channel size; based on the sample; between about 1-20 µm such as 1, 2, 5, 8, 10, 12, 15, 17, 20 µm; ≥20 µm; ≤1 µm; etc.) and/or have any size. The control particles can be included in any ratio to the sample between about 1:10,000 to 1:1 such as 1:1,000; however, the ratio can be less than 1:10,000; greater than 1:1; and/or any ratio. The flow guide preferably receives at least 100 cells per second, such as 200, 300, 500, 1000, 1500, 2000, 2500, 3000, 5000, 10000, 100-10000 cells per second, but can receive more than 10,000 cells per second, less than 100 cells per second, a variable number of cells per second, and/or any number of cells.

The sample can be received automatically (e.g., using an autosampler, robot, etc.) and/or manually (e.g., provided by an operator). The sample is preferably received at an inlet of the microfluidic device, but can be received at a focusing region, a deformation region, a sample preparation device, and/or at any suitable region and/or component of a cytometry system. The received sample can be processed and/or unprocessed (e.g., as collected such as drawn from the patient).

Figure 6:
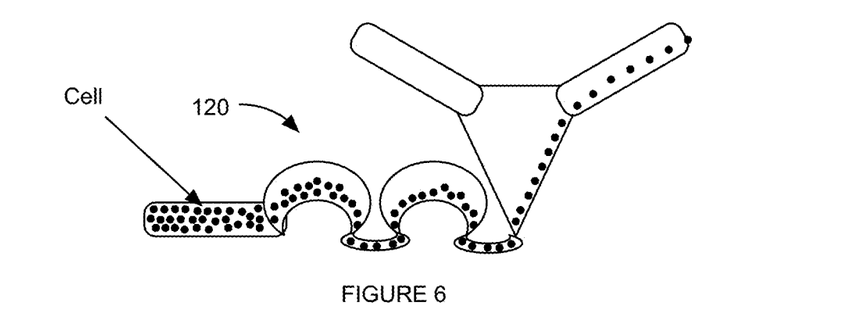
FIG. 6 is a schematic representation of an example of focusing and/or aligning cells in a focusing region of a microfluidic device.

Transporting the sample S300 within the microfluidic device functions to focus and/or align the sample (and/or constituents thereof) and/or to transport the sample from the inlet to a deformation region. As shown for example in FIG. 6, focusing and/or aligning the sample can separate constituents so that the majority of the time (e.g., 70%, 80%, 90%, 95%, 99%, 100%, etc. of the time) a single constituent is in the deformation region, can separate constituents so that the majority of constituents (e.g., 50%, 60%, 70%, 75%, 80%, 90%, 95%, 99%, 100%, etc.) enter a single flow channel, and/or can otherwise transport the sample. The sample is preferably transported in sheath fluid within the microfluidic device, but can be suspended in any medium. The focusing and/or aligning is preferably performed in a focusing region of the microfluidic device, but can be performed in any region of the microfluidic device and/or by any component. Aligning and/or focusing the sample are preferably performed passively (e.g., within one or more focusing regions of the microfluidic device such as based on the shape and/or structure of the focusing region), but can be performed actively (e.g., using a pump, gating, etc.).

Figure 4:
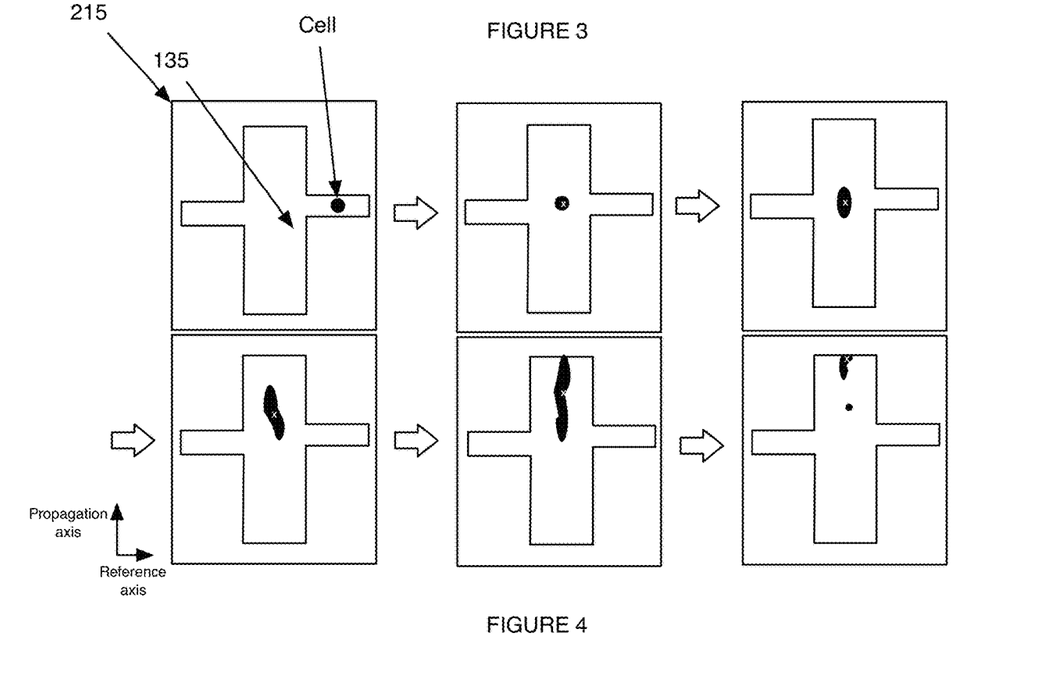
FIG. 4 is a schematic representation of an example of acquiring a plurality of images of a cell before, during, and after a force is applied to the cell and determining a centroid of the cell for each image of the plurality of images as shown in this example by the 'x' character.

Applying a force S400 to the sample functions to apply a stress (and/or strain) to the sample, where the force functions to deform (e.g., compress, expand, distort, reconfigure, as shown for example in FIGS. 4 and 7, etc.), perturb, and/or damage the sample (and/or constituents thereof). The force can cause elastic or inelastic deformation of the sample. The force is preferably applied to each constituent (e.g., each cell, each particle, etc.) individually (e.g., a single constituent is within the deformation region at a time). However, the force can be applied to a plurality of constituents and/or the entire sample simultaneously. The force applied to the sample can depend on: the transport medium (e.g., sheath fluid), the microfluidic device temperature, the fluid temperature, the flow rate, the fluid pressure, the microfluid channel size (e.g., width, depth), the microfluidic channel shape, the arrangement of the deformation region, and/or on any parameters, each of which can be measured and/or controlled to adjust the deformation conditions.

The force applied to each constituent is preferably substantially identical (e.g., varies by at most 5%, 10%, 20%, 25%, 30%, etc.), however, the force applied to each constituent can be different. The force is preferably applied proximal to and/or within the deformation region (e.g., proximal to the stagnation point of the deformation region) of the microfluidic device, but can be applied at any location. The force is preferably applied by an intersection of fluid flow between two or more channels proximal the deformation region. In some variants, the force can be applied asymmetrically to the constituents. In an illustrative example, the fluid flow intersection can be asymmetric (e.g., can have a nonzero vorticity) causing a differential force to be felt along a first region of the constituent and a second region of the constituent. In a second specific example, the flow rate and/or channel size for each of the intersecting channels proximal the deformation region can be different. However, the force can be applied asymmetrically in any manner.

In variants, the control particles included within the sample can be used to determine (e.g., estimate, measure, calculate, etc.) the force that is being applied (e.g., based on a deformation measured in the control particles). In a first specific example, the force can be modified (e.g., by changing a flow rate, flow volume, fluid pressure, temperature, channel size, etc.) based on a force determined by the control particles. In a second specific example, the datasets can be processed (e.g., interpolated, transformed, discarded, etc.) to correct for a variation of force overtime as determined based on the control particles.

In a first specific example, the force is applied by diverting a first portion of the sample volume in a first flow and a second portion of the sample volume in a second flow substantially opposed to the first flow; intersecting the first and second flows to cooperatively define a deformation region therebetween; and delivering the constituent(s) to the deformation region (e.g., via the first, second, or separate flow). In a second example, the force is applied by intersecting a first and second flow (e.g., of non-sample fluid) to cooperatively define a deformation region, and delivering the constituent(s) to the deformation region via a third flow. However, the force can be otherwise applied.

Acquiring a dataset S500 preferably functions to measure a dataset associated with the sample. The dataset can be acquired and/or include data before, during, and/or after the force is applied. The dataset preferably includes a plurality of images (e.g., an optical dataset such as collected using a camera or image acquisition system; a thermal dataset such as acquired using an infrared camera; etc.), but can additionally or alternatively include electrical data (e.g., resistance, conductivity, etc.), thermal data, probe measurements (e.g., a probe in contact with the sample, a probe in contact with the microfluidic channel(s), a probe in contact with the sheath fluid, etc.), pressure measurements, force measurements, and/or any suitable data. The dataset preferably includes data associated with each constituent of the sample, but can include data associated with a subset of the constituents of the sample, the sample as a whole, and/or any suitable data. The dataset is preferably acquired by a detection system (e.g., an image acquisition system, a camera, etc.), but can be performed by a computing system and/or by any suitable component.

The plurality of images of each constituent preferably includes at least ten images of the constituent, but can include fewer than ten images (e.g., between one to nine images) of the constituent. The plurality of images preferably include images before, during, and after the force is applied. However, the plurality of images can correspond to images before, before and during, before and after, during, during and after, and/or after the force has been applied.

Determining one or more features S600 functions to determine (e.g. identify, extract, etc.) one or more features from the dataset. The feature is preferably an object within the images (e.g., a cell, a cell fragment, a cell component, a control particle, a contaminant, etc.). However, the feature can be a portion of the object (e.g., cell nucleus, bacteria, organelle, etc.), the object can be related to the feature (e.g., by a transformation), and/or the feature can be otherwise determined from the object and/or the images. The features are preferably determined by a computing system (e.g., a feature module of a computing system), but can be performed by any component.

Figure 8:
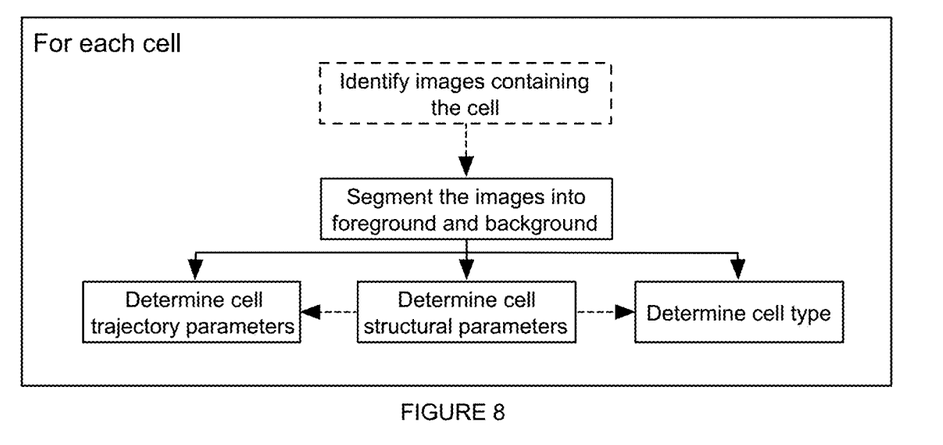
FIG. 8 is a flow chart of an example of determining features and a set of parameters for each cell of a sample.

Determining the features can include: detecting a constituent, segmenting an image, identifying the constituent, and/or any steps. An example is shown in FIG. 8.

Detecting a constituent functions to determine whether a constituent is present in a given image. Detecting a constituent can be particularly beneficial for embodiments of the method that capture a large number of images without constituents present and thus need to sort or identify which images contain a constituent, but can be performed for any embodiment of the method. Detecting a constituent can be performed for every image and/or for a subset of images. For example, when a constituent is detected in a first image, N (where N is an integer such as 1, 2, 5, 10, 20, 50, 100, etc.) subsequent images can be considered to include the same constituent. Detecting a constituent can be performed using object detectors, machine learning techniques (e.g., Viola-Jones object detection, Scale-invariant feature transform (SIFT), Histogram of oriented gradients (HOG), etc.), deep learning techniques (e.g., Region Proposals such as R-CNN, Fast R-CNN, Faster R-CNN, cascade R-CNN, etc.; Single Shot MultiBox Detector; You Only Look Once; Single-Shot Refinement Neural Network for Object Detection; Retina-Net; deformable convolutional networks; etc.), object tracking techniques (e.g., optic flow), and/or be otherwise performed.

Segmenting an image functions to identify the pixels associated with the constituent (e.g., object of interest). In a first variation, segmenting the image can include: foreground/background segmentation to separate each image (e.g., each image that includes a constituent, each image, etc.) into a foreground (e.g., the constituent) and a background (e.g., the rest of the image). In a second variation, segmenting the image can include applying semantic segmentation to identify the cell pixels (e.g., segmented blob) and determine the cell type (e.g., cell subpopulation) associated with the segmented blob. Segmenting an image can be performed using thresholding, k-means clustering, histogram-based image segmentation, edge detection, motion-based segmentation, deep learning techniques (e.g., convolutional neural networks, fully convolutional networks, ensemble learning, etc.), and/or otherwise segment the image.

Identifying the constituent can function to characterize and/or classify the constituent (e.g., constituent type). In an illustrative example, identifying the constituent can determine whether the constituent in the image is a cell or not a cell (e.g., a control particle, dust, contaminant, etc.). In a second illustrative example, identifying the constituent can determine what kind of cell is in the image (e.g., granulocyte or agranulocyte; myleoid or lymphoid; erythrocyte or leukocyte; neutrophils, eosinophils, basophils, lymphocytes, or monocytes; etc.). The constituent can be identified based on an object parameter (e.g., object color, object brightness, object contrast, etc.), based on an object size (e.g., constituent volume, length, width, and/or height; size of an internal structure such as nucleus size; presence of internal structures such as organelles; etc.), based on the feature values extracted from the dataset, based on the portion of the fractionated blood, based on the auxiliary information, and/or based on any information. The constituents are preferably identified automatically (e.g., using semantic segmentation, classification, convolutional neural networks, fully convolutional networks, deep learning, machine learning, etc.), but can be identified manually (e.g., by a user, operator, patient, technician, etc.). The constituents can be identified based on visual features, parameters (e.g., aspect ratios), expression (e.g., antibody affinity, fluorescence, etc.), and/or otherwise determined. In variants, identifying the constituent can determine a probability that the object in the foreground corresponds to a class, assign a class to the object, and/or otherwise classify the object.

Determining a set of parameters S700 functions to determine a set of constituent parameters (e.g., cell parameters, metrics, descriptors, etc.)) based on the features and/or the dataset, where the set of parameters are preferably associated with (e.g., correlated with, related to, etc.) a health state of a patient. The constituent parameters can correspond to (e.g., are determined from, are extracted from) features, be determined based on (e.g., calculated from, derived from, etc.) the features, be determined based on the dataset, and/or be otherwise determined. The constituent parameters can correspond to constituent features at specific positions within the channel, times relative to the applied force (e.g., before the force is applied, while the force is applied, after the force is applied), relative to the applied force parameters (e.g., magnitude, direction, duration etc.), average properties (e.g., average properties across all images containing the same constituent), conserved properties (e.g., properties that remain the same throughout the images of the constituent), changing properties (e.g., properties that change throughout the images of the constituent), derived and/or extracted properties (e.g., a parameter generated by examining two or more images of the constituent; a parameter generated based on a difference relative to a 'master,' expected, average, etc. constituent; etc.), and/or correspond to any suitable feature or property. Parameters can correspond to the sample, one or more constituents thereof, a patient and/or user, and/or correspond to any source. One or more parameters of the set of constituent parameters can be associated with (e.g., correlated with, depend on) one or more factors, such as: a stiffness of a constituent (e.g., Young's modulus), antibody expression state, cell type, density of the sample, a density of a constituent (e.g., density of the cell), average density of the constituents within the sample, constituent mass, constituent volume, collection parameters, and/or other factors (e.g., wherein the patient health condition is determined based on a constituent parameter associated with the factor). The parameter(s) can be associated with the factors parametrically, can be related to the factors according to an equation (e.g., a linear relationship, a nonlinear relationship, etc.), can be correlated with the factors, and/or can be otherwise associated with the factors. The set of parameters are preferably determined by a computing system (e.g., a parameter module of a computing system), but can be determined manually (e.g., by a user, operator, technician, patient, etc.) and/or by determined by any component.

The set of constituent parameters preferably correspond to population parameters (e.g., parameters that are representative of the sample), but can correspond to and/or be associated with an event parameters (e.g., parameters that are representative of an image such as parameters determined based on a feature or object within the image; parameters that are representative of a constituent such as parameters determined based on a plurality of images of a constituent, a feature, an object, etc.; etc.) and/or correspond to any suitable reference. The population parameters are preferably determined from event parameters, but can be otherwise determined. The population parameters can be an average of a plurality of event parameters, a characteristic parameter (e.g., maximum, minimum, mean, median, mode, etc.) of the event parameters, and/or can be otherwise related to the event parameters. In specific example, determining one or more parameters of the set of parameters can include: averaging the parameters determined for each event (e.g., image, constituent traversal through the device or deformation region, etc.), averaging the parameters that exceed a threshold (e.g., averaging the parameters that are greater than the $10^{th}$, $20^{th}$, $30^{th}$, $40^{th}$, $50^{th}$, $60^{th}$, $70^{th}$, $80^{th}$, $90^{th}$, $95^{th}$, etc. percentile, averaging the parameters that are less than the $5^{th}$, $10^{th}$, $20^{th}$, $30^{th}$, $40^{th}$, $50^{th}$, $60^{th}$, $70^{th}$, $80^{th}$, $90^{th}$, $95^{th}$, etc. percentile, etc.), averaging a subset of the parameters (e.g., parameters associated with the same feature type such as the same cell type), an extrema parameter (e.g., maximum, minimum, etc.), determining a correlation between parameters, determining a variance and/or standard deviation of the set (or a subset) of the event parameters, using an equation relating the event parameters to the population parameters, using a weighted average of the event parameters, and/or can be otherwise determined.

A different set of parameters is preferably calculated for each cell type (e.g., each cell subpopulation); alternatively, a single set of parameters can be calculated for the cell population (e.g., all leukocytes), for a combination of cell populations, or otherwise determined.

In variants, the set of constituent parameters can include: structural parameters, trajectory parameters, sample parameters (e.g., patient parameters), location parameters (e.g., cell position relative to the image frame, relative to the channel, relative to the outlet, relative to the inlet, relative to the stagnation point, etc.), and/or any parameters. Trajectory parameters can be parameters that are associated with and/or determined from the trajectory of the cell through the microfluidic device (e.g., the deformation region of the microfluidic device, the focusing region, etc.). The trajectory can be a series of discrete positions (e.g., of the centroid, of the center of mass, of a reference point, average position of the cell, etc.) of the cell, a continuous path of the cell, and/or correspond to any motion of the cells as they pass through the fluid flow (e.g., deformation region of the microfluidic device).

Figure 5:
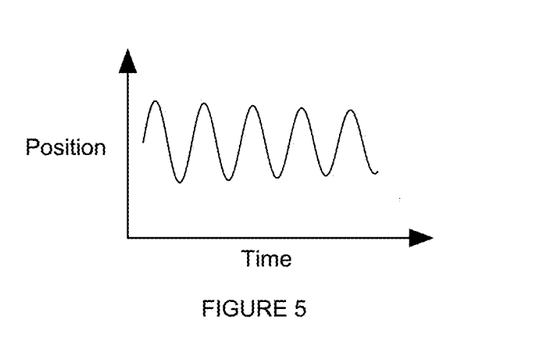
FIG. 5 is a schematic representation of an example of a measured oscillation of a centroid of the cell in FIG. 4 relative to the stagnation point along a reference axis.

Examples of structural parameters include: shape (e.g., ellipticity, helicity, oblongness, circularity, curvature, skewness, etc.), aspect ratio (e.g., ratio of longest dimension to shortest dimension, ratio of length to width, etc.), size (e.g., lateral extent, longitudinal extent, depth, height, width, length, volume, surface area, etc.), constituent structure (e.g., cell membrane location, cell shape, cell wall structure, etc.), constituent morphology (e.g., cell morphology, cell shape, particle shape, etc.), internal structure (e.g., shape, morphology, size, etc. of a nucleus and/or other organelle of a cell), and/or any other structural parameters Examples of trajectory parameters include: direction of object and/or feature motion, speed of object and/or feature motion (e.g., average speed, instantaneous speed, etc.), acceleration of object and/or feature motion, an oscillation in the object and/or feature motion (e.g., an amplitude of the oscillation, a frequency of the oscillation, a phase of the oscillation, a modulation in the oscillation, a decay of the oscillation, as shown for example in FIG. 5, etc.), viscoelastic inertial response (VEIR), a deviation in the particle flow trajectory (e.g., from a linear path, an expected path, etc.), and/or any other trajectory parameters. The trajectory parameters can be determined based on a difference, sum, amplitude, maximum, minimum, average value of, and/or other characteristic of one or more positions of the trajectory. In variations where the trajectory parameters include an oscillation, the oscillation can correspond to an oscillation of a reference point (e.g., centroid, extrema, etc.), a reference axis (e.g., one or more dimension such as length, width, depth), one or more reference surface (e.g., object boundary, interior boundary of the object such as corresponding to an organelle boundary, etc.), reference volume (e.g., object volume, internal structure of the object, etc.), and/or other portion of the object. The oscillation preferably occurs along a reference axis perpendicular to the direction of motion of the object. However, the reference axis can be parallel to the direction of motion and/or have any orientation relative to the direction of motion. The oscillation amplitude is preferably on the micron-size scale (e.g., 1-10 μm, 10-100 μm, etc.), but can additionally or alternatively be nanometer scale (e.g., 1-100 nm, 100 nm-1 μm, etc.) and/or be any suitable distance. In a specific example, the VEIR for a cell can be determined based on the oscillation amplitude, and can optionally be determined based on the deformation conditions, the cell type, and/or any other suitable information.

Examples of sample parameters (e.g., patient parameters) include: complete particle count, complete blood count, complete leukocyte count, complete neutrophil count, complete monocyte count, complete lymphocyte count, complete basophil count, complete eosinophil count, complete erythrocyte count, complete platelet count, constituent numerosity (e.g., number of cells and/or segments of cells, number of particles and/or segments of particles, etc.), presenting symptoms (e.g., patient temperature, blood pressure, weight, blood oxygenation, etc.), cell density, cell culture results, hydration, and/or any other sample parameters.

Determining the set of parameters can include calculating an average of one or more measurements, fitting a dataset (e.g., to an equation where one or more fit parameters of the equation can correspond to one or more parameters of the set of parameters, to a shape, etc.), determining a location and/or region of an image including the feature (and/or a subset of the feature), using machine learning techniques, performing a transformation on the dataset, and/or any steps.

In an illustrative example, determining a structural parameter can include determining a boundary of the feature (e.g., interior boundary, exterior boundary, etc.) and determining a structural parameter based on the boundary. In a first variation of this illustrative example, the structural parameter can be determined based on the known geometry of the detection system and the sample geometry (e.g., the size of the feature can be determined based on the system geometry and known camera parameters such as focal distance, optical sensor size, etc.). In a second variation of this illustrative example, the structural parameter can be determined by determining a disparity map between two images that include the same feature. In a specific example, the aspect ratio of the cell in each frame and/or position along the deformation region can be determined based on the cell dimensions extracted from the respective frames.

In an illustrative example, determining a trajectory parameter can include: determining a centroid position of the feature (e.g., object, constituent) in each image of the plurality of images, tracking a change in position of the centroid between the plurality of images, measuring an amplitude of an oscillation (e.g., using a one or more peaks or cycles of the oscillation), and calculating a parameter based on the amplitude of the oscillation. In a first variation of this illustrative example, measuring the amplitude can exclude measuring the amplitude of the first, second, and/or any suitable peaks of the oscillation, which can enhance the reproducibility of the measurements. In a second variation of this illustrative example, measuring the amplitude can include measuring the amplitude of the third, fourth, fifth and/or any peaks of the oscillation and averaging the amplitudes to determine the fit parameter. In a third variation of this illustrative example, measuring the amplitude can include measuring the amplitude of the third, fourth, fifth and/or any peaks of the oscillation and fitting the oscillation to a predetermined equation (e.g., an oscillatory function such as trigonometric function, a damped oscillation, an exponential function, etc.) to determine a trajectory parameter (e.g., a fit parameter such as amplitude, offset, phase, frequency, decay, damping, driving, etc.). In a fourth variation of this illustrative example, the trajectory parameter can include one or more Fourier coefficients from a Fourier decomposition (e.g., a Fourier cosine transformation, Fourier sine transformation, Fourier transformation, etc.) of the trajectory. In a fifth variation of this specific example, the trajectory parameter can be determined based on a change in a structural parameter between images that contain the same feature. In a specific example, the VEIR of the cell during flow through the deformation region can be determined based on the cell oscillation amplitude extracted from the respective timeseries of frames. In a sixth variant of this illustrative example, the trajectory parameter can be determined based on the amplitude of a primary, secondary, ternary, quaternary, quintenary (quinary), senary, septenary, octonary, nonary, denary cycle, and/or other cycle of the oscillation, and/or a combination of the above (e.g., excluding some cycles, such as the primary and/or secondary cycles; including a subset of cycles, such as only the ternary, quaternary, and quintenary cycles; etc.). However, the trajectory parameter can be otherwise determined.

Determining a health state of a patient S800 functions to determine (e.g., diagnose) a health state of the patient based on the set of parameters (e.g., the population parameters, event parameters). The health state can include: an immune activation state (e.g., systemic inflammatory response syndrome (SIRS)), blood cell health, organ health, cancer condition, inflammation, health conditions (e.g., sepsis, sepsis-related condition, anemia, bleeding conditions, etc.), and/or any suitable health status of the patient. In some variations, the health state can be caused by and/or include a diagnosis of (e.g., a probability that the health state is caused by) one or more pathogens (e.g., bacteria, virus, fungi, chemicals, etc. such as class of pathogen, specific pathogens, etc.) and/or other causes of the health state. In an illustrative example, the health state can be an immune activation state associated with a patient's immune response to the novel coronavirus virus SARS-CoV-2 ("COVID-19"). The health state can be a binary state (e.g., yes or no whether the patient is positive for a given health state), a severity index (e.g., 'healthy,' 'no indications,' 'mild,' 'moderate,' 'severe,' 'critical,' 'acute,' 'life-threatening,' etc.), a numerical value, a probability and/or likelihood that the patient has a condition, and/or other representation of a health state.

In examples, the determined index or health state can optionally be used to: track the patient's disease state progression over time, determine a treatment parameter (e.g., estimated hospital stay duration, estimated triage requirements, etc.), initiate secondary analyses, and/or otherwise used. Examples of secondary analyses include: innate immune activation assays, such as light microscopy to assay structural features, cytology assays, chemical change assays (e.g., using immunofluorescence labeling of CD11b, CD18, CD64, CD66b, and/or other markers and flow cytometry), transcriptomic signatures analyses, and/or other analyses.

The health state is preferably determined automatically (e.g., responsive to determination of a set of parameters), but can be determined semi-automatically (e.g., responsive to a health professional request for a diagnosis or probabilistic diagnosis) and/or manually (e.g., by a health professional). The health state is preferably determined by a computing system (e.g., a diagnosis module of a computing system), but can be determined by any component.

The health state can be determined from a model, an equation, a look-up table, a neural network (e.g., trained to output a score, trained to output a disease state, etc.), and/or otherwise be determined. Examples of models that can be used include: logistic regressions (e.g., linear logistic regressions, nonlinear logistic regressions, etc.), decision trees, Bayesian classifiers, nearest neighbor techniques, support vector machines, decision forests (e.g., random forest), neural networks, gradient boosting, and/or any model can be used. The model can be: a predetermined model, a general model, a model selected based on the auxiliary information, and/or any other suitable model.

Inputs to the model can include: one or more parameter from the set of parameters; auxiliary information such as age, maturity (e.g., adolescent or adult), weight, height, race, sex, temperature, body mass index, body fat ratio, preexisting conditions, duration of symptoms, onset of symptoms, travel, blood oxygenation levels, blood pressure, infection source, etc.; treatment parameters (e.g., hospital stay; administered treatments; etc.); collection parameters (e.g., temperature; other compounds found in the sample; etc.); and/or any inputs. In an illustrative example, the inputs can include a trajectory parameter (e.g., an oscillation amplitude), a cell size (e.g., thickness), and a cell enumeration (e.g., number of neutrophils, number of leukocytes, etc.).

Outputs of the model can include: an index (e.g., a health status index; a leukocyte structural index (LSI); a value between 0-1, 0-10, etc.; a score; a number of constituents with a parameter and/or combination of parameters that exceeds a threshold such as the total number of constituents exceeding the threshold, a fraction of the total number of constituents exceeding the threshold, etc.; a probability; etc.), a health status, a health status severity, a probability of a health status, and/or any output.

In an illustrative example, the health status can be determined based on the index. When the index exceeds a threshold (e.g., 0.01, 0.05, 0.1, 0.2, 0.25, 0.3, 0.4, 0.5, 0.6, 0.7, 0.75, 0.8, 0.9, 0.95, 0.99, 1, etc.), the health status can indicate that a patient has (or is likely to have such as probability at least 50%) a condition. When the index is below a threshold (e.g., 0.01, 0.05, 0.1, 0.2, 0.25, 0.3, 0.4, 0.5, 0.6, 0.7, 0.75, 0.8, 0.9, 0.85, 0.99, 1, etc.), the health status can indicate that a patient does not have a condition (or is likely to not such as the probability that the patient does not have the condition is at least 50%). However, the index falling below a threshold can be indicative of a condition, the index exceeding a threshold can be indicative of not having a condition, and/or the index can be used in any manner. The threshold can be determined based on a training dataset (e.g., in a similar manner to how the model is generated, in a similar manner to how the inputs to the model are selected), be predetermined, be determined according to an equation (e.g., an equation based on and/or that accounts for the auxiliary sample information), and/or can be otherwise determined.

In some variants, a single index can be determined (e.g., wherein the population parameters for each cell subpopulation can be aggregated into a single calculation). In other variants, more than one index can be determined for a patient and/or sample. For example, a neutrophil index and a monocyte index can be determined. Each index can have the same threshold or a different threshold. For example, a monocyte index exceeding a threshold of 0.75 can be indicative of a condition and a neutrophil index exceeding a threshold of 0.9 can be indicative of a condition. When a plurality of indices are used, the health status can be determined based on voting, a preferred index, a weighted average of the indices results, an equation relating the indices and/or thresholds, and/or be otherwise determined.

The model inputs and/or the threshold are preferably determined based on a training dataset. The training dataset is preferably associated with a patient cohort that has been diagnosed with and/or otherwise determined to have a condition (e.g., a high sepsis incidence). However, any patient cohort can be used. Machine learning techniques (e.g., a neural network) are preferably used to determined (e.g., which inputs, combination of inputs (e.g., linear combinations, nonlinear combinations, etc.), and/or threshold(s) are correlated with the predetermined health status. However, the inputs, combination of inputs, and/or thresholds can be determined empirically, using a regression (e.g., linear regression, nonlinear regression), manually, and/or can be otherwise determined. In some variants, the inputs, combination of inputs, and/or thresholds can be validated (e.g., determines that the inputs, combination of inputs, and/or threshold determined from the training dataset indicate that the control group does not or is unlikely to have the condition) using a control group (e.g., a cohort of patients that do not have and/or are unlikely to have the condition).

The method and/or steps thereof can include performing one or more steps of operating a microfluidic device and/or cytometry system as disclosed in U.S. application Ser. No. 16/374,663 filed 3 Apr. 2019 and entitled 'SYSTEM AND METHOD FOR DEFORMING AND ANALYZING PARTICLES,' U.S. application Ser. No. 15/868,025 filed 11 Jan. 2018 entitled 'METHOD AND DEVICE FOR HIGH THROUGHPUT CELL DEFORMABILITY MEASUREMENTS,' U.S. application Ser. No. 16/676,352 filed 6 Nov. 2019 entitled 'METHOD AND DEVICE FOR HIGH-THROUGHPUT SOLUTION EXCHANGE FOR CELL AND PARTICLE SUSPENSIONS,' U.S. Pat. No. 9,464,977 filed 18 Oct. 2013 entitled 'SYSTEM AND METHOD FOR DEFORMING, IMAGING AND ANALYZING PARTICLES,' U.S. Pat. No. 10,252,260 filed 3 Apr. 2017 entitled 'SYSTEM AND METHOD FOR DEFORMING PARTICLES,' each of which is incorporated herein in its entirety by this reference.

In a first example, the method includes: receiving images of cells (e.g., leukocytes) during deformation; for each cell, extracting cell features from the images (e.g., dimensions and position within the flow region); for each cell, determining a trajectory parameter (e.g., oscillation amplitude) and/or a structural parameter (e.g., aspect ratio) based on the cell features; calculating an index based on the trajectory parameter and/or structural parameter values; and determining a health condition of the patient based on the index. The method can optionally include separating the cell data according to cell subpopulation (e.g., monocyte, lymphocyte, neutrophil), wherein the index can be calculated based on the parameters for a subset of the cell subpopulations (e.g., monocytes and neutrophils).

In a second example, the system can include a computing system configured to perform the method described in the first and/or second example. The system can optionally include a microfluidic device.

Embodiments of the system and/or method can include every combination and permutation of the various system components and the various method processes, wherein one or more instances of the method and/or processes described herein can be performed asynchronously (e.g., sequentially), concurrently (e.g., in parallel), or in any other suitable order by and/or using one or more instances of the systems, elements, and/or entities described herein.

As a person skilled in the art will recognize from the previous detailed description and from the figures and claims, modifications and changes can be made to the preferred embodiments of the invention without departing from the scope of this invention defined in the following claims.

We claim:

1. A method comprising:
   receiving a plurality of blood cells from a patient;
   for each blood cell of the plurality of blood cells, determining biophysical parameters based on an oscillation of the blood cell as the blood cell is deformed, wherein the oscillation occurs while the blood cell is moving along a channel, wherein the oscillation occurs in a direction perpendicular to a longitudinal axis of the channel;
   computing an index from the biophysical parameters using a logistic regression; and
   within at most a threshold time of receiving the plurality of blood cells, determining an immune activation of the patient based on the index.

2. The method of claim 1, wherein, for each blood cell of the plurality of blood cells, determining the biophysical parameters comprises:
   deforming the blood cell within a deformation region of a microfluidic chip; and
   extracting features from a plurality of images acquired before the blood cell enters and as the blood cell passes through the deformation region.

3. The method of claim 1, wherein, for each blood cell of the plurality of blood cells, the biophysical parameters are determined from a trajectory of the blood cell as the blood cell is deformed.

4. The method of claim 3, wherein, for each blood cell of the plurality of blood cells, the oscillation comprises an oscillation of a reference point of the blood cell, wherein the biophysical parameters comprise an amplitude of the oscillation of the reference point of the blood cell as the blood cell is deformed.

5. The method of claim 4, wherein the reference point comprises a centroid of the blood cell.

6. The method of claim 3, wherein, for each blood cell of the plurality of blood cells, the biophysical parameters further comprise structural parameters of the blood cell.

7. The method of claim 6, wherein the structural parameters comprise a cell size or a cell aspect ratio.

8. The method of claim 6, wherein the structural parameters comprise structural parameters before and as the blood cell is deformed.

9. The method of claim 1, wherein the logistic regression is trained to classify the immune activation based on measurements from a high acuity patient cohort.

10. The method of claim 1, wherein the threshold time is at most 10 minutes.

11. The method of claim 1, wherein the immune activation comprises a sepsis condition.

12. A method comprising:
   receiving a plurality of blood cells from a patient;
   for each blood cell of the plurality of blood cells, determining biophysical parameters based on an oscillation of the blood cell, the oscillation occurring while the blood cell is in motion, wherein the oscillation occurs in a direction orthogonal to a direction of the motion; and
   within at most a threshold time of receiving the plurality of blood cells, determining an immune activation of the patient based on the biophysical parameters for the plurality of blood cells.

13. The method of claim 12, wherein, for each blood cell of the plurality of blood cells, the biophysical parameters are determined based on an amplitude of the oscillation of the blood cell.

14. The method of claim 12, wherein, for each blood cell of the plurality of blood cells, the oscillation of the blood cell comprises an oscillation of a centroid of the blood cell.

15. The method of claim 12, wherein the biophysical parameters are determined without using a first cycle of the oscillation.

* * * * *